(12) United States Patent
Zhang et al.

(10) Patent No.: US 9,895,122 B2
(45) Date of Patent: Feb. 20, 2018

(54) SCANNING APPARATUS, MEDICAL IMAGE DEVICE AND SCANNING METHOD

(71) Applicant: Toshiba Medical Systems Corporation, Otawara-shi (JP)

(72) Inventors: Bowen Zhang, Beijing (CN); Jianchun Zhao, Beijing (CN)

(73) Assignee: Toshiba Medical Systems Corporation, Otawara (JP)

( * ) Notice: Subject to any disclaimer, the term of this patent is extended or adjusted under 35 U.S.C. 154(b) by 330 days.

(21) Appl. No.: 14/276,024

(22) Filed: May 13, 2014

(65) Prior Publication Data
US 2014/0336504 A1  Nov. 13, 2014

(30) Foreign Application Priority Data

May 13, 2013  (CN) .......................... 2013 1 0174259

(51) Int. Cl.
| | |
|---|---|
| G06K 9/00 | (2006.01) |
| A61B 6/00 | (2006.01) |
| A61B 6/03 | (2006.01) |
| A61B 5/055 | (2006.01) |
| A61B 5/00 | (2006.01) |
| G06T 7/73 | (2017.01) |
| G06T 7/13 | (2017.01) |

(52) U.S. Cl.
CPC .............. *A61B 6/505* (2013.01); *A61B 5/055* (2013.01); *A61B 5/4585* (2013.01); *A61B 6/032* (2013.01); *A61B 6/037* (2013.01); *A61B 6/5217* (2013.01); *A61B 6/54* (2013.01); *G06T 7/13* (2017.01); *G06T 7/73* (2017.01); *G06T 2207/10072* (2013.01); *G06T 2207/30008* (2013.01)

(58) Field of Classification Search
CPC ..... A61B 5/0037; A61B 5/055; A61B 5/4528; A61B 5/4533; A61B 2576/026; A61B 5/4585; A61B 5/0042; A61B 6/505; A61B 6/032; A61B 6/037; A61B 6/54; A61B 6/5217; G01R 33/4833; G01R 33/546; G01R 33/543; G06T 7/73; G06T 7/13; G06T 2207/10072; G06T 2207/30008
See application file for complete search history.

(56) References Cited

U.S. PATENT DOCUMENTS

2010/0121175 A1    5/2010  Jolly et al.
2012/0093385 A1*   4/2012  Yokosawa ............ A61B 5/0037
                                                            382/131

* cited by examiner

*Primary Examiner* — Elmer Chao
(74) *Attorney, Agent, or Firm* — Oblon, McClelland, Maier & Neustadt, L.L.P.

(57) ABSTRACT

A scanning apparatus according to an embodiment includes a first scanning control unit, a first determination unit, a second scanning control unit, a second determination unit, and a third scanning control unit. The first scanning control unit obtains at least one first slice image of the leg in an approximate coronal plane direction. The first determination unit determines a direction of a gap between a thighbone and a shinbone in the at least one first slice image. The second scanning control unit obtains at least one second slice image of the leg in a direction vertical to the direction of the gap in the at least one first slice image. The second determination unit determines an axial plane direction according to the at least one second slice image. The third scanning control unit obtains at least one slice image of the leg in the axial plane direction.

12 Claims, 8 Drawing Sheets

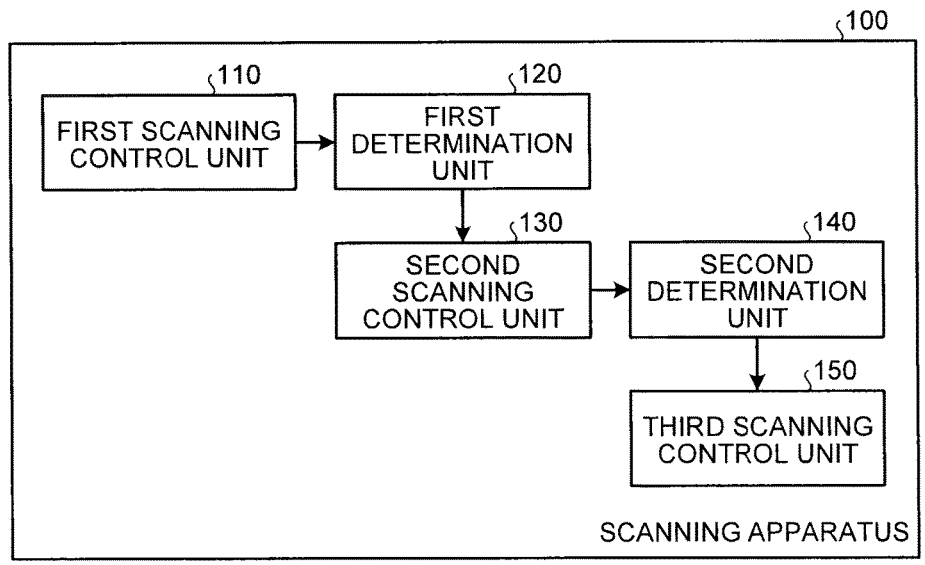
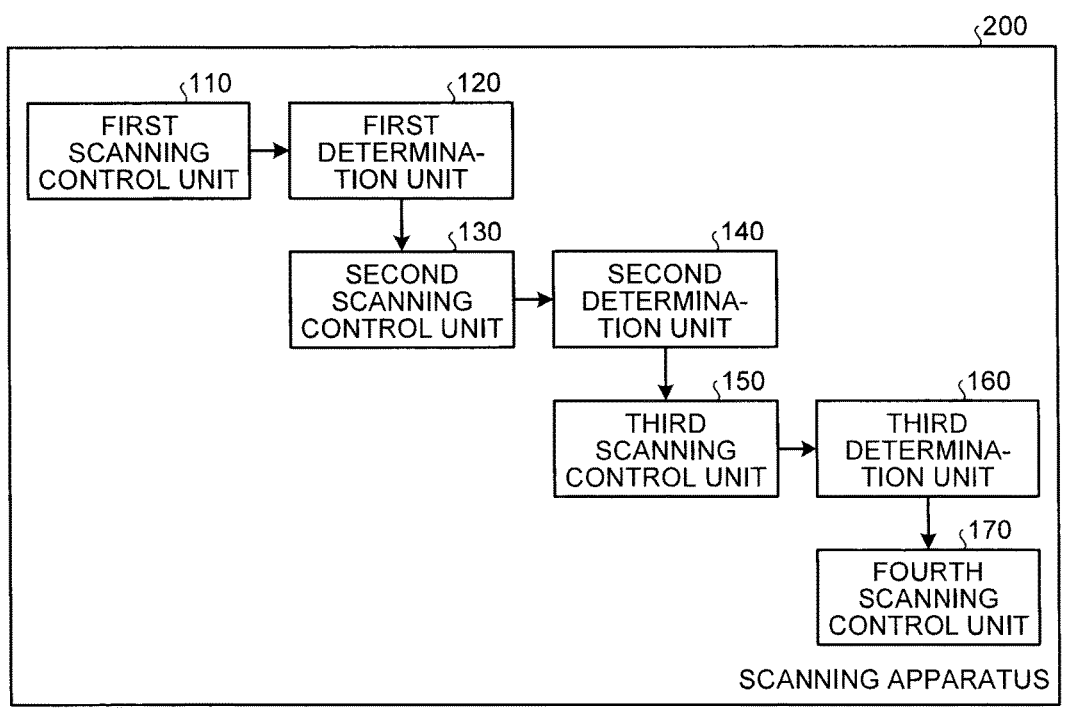

SCANNING APPARATUS, MEDICAL IMAGE DEVICE AND SCANNING METHOD

CROSS-REFERENCE TO RELATED APPLICATIONS

This application is based upon and claims the benefit of priority from Chinese Patent Application No. 201310174259.3, filed on May 13, 2013, the entire contents of which are incorporated herein by reference.

FIELD

The present invention relates to the field of information processing and more particularly to a scanning apparatus, a medical image device and a scanning method.

BACKGROUND

Positioning scanning is usually needed when a leg is scanned to observe a specific part. Many positioning scanning methods are currently available. There is a technology based on three-dimensional (3D) data in which a 3D image of a leg in a predetermined positioned scanning direction is obtained by a 3D imaging device, an approximate position of a knee joint in the generated image is determined, a volume of interest at the approximate position is defined, and the volume of interest divided to obtain the image of the thighbone on the knee joint, a posterior condyle line (PCL) is detected, and a positioning scanning is performed on the leg.

However, the technology based on 3D data spends a long time to obtain 3D data in most cases, and the segmentation based on 3D data is extremely sensitive to noises, segmentation thresholds, image quality and scanning parameters and the like.

Therefore, a technology capable of addressing the above problem is desired.

BRIEF DESCRIPTION OF THE DRAWINGS

The above-mentioned and other objects, characteristics and advantages of the present invention will be more readily understood by reference to the description of embodiments of the present invention made in conjunction with accompanying drawings, in which elements are merely illustrative of the principle of the present invention, and identical or similar reference signs designate identical or similar technical features or elements.

FIG. 1 is a block diagram illustrating an exemplary configuration of a scanning apparatus according to an embodiment of the present invention;

FIG. 2 is a block diagram illustrating an exemplary configuration of a scanning apparatus according to another embodiment of the present invention;

DETAILED DESCRIPTION

Figure 3:
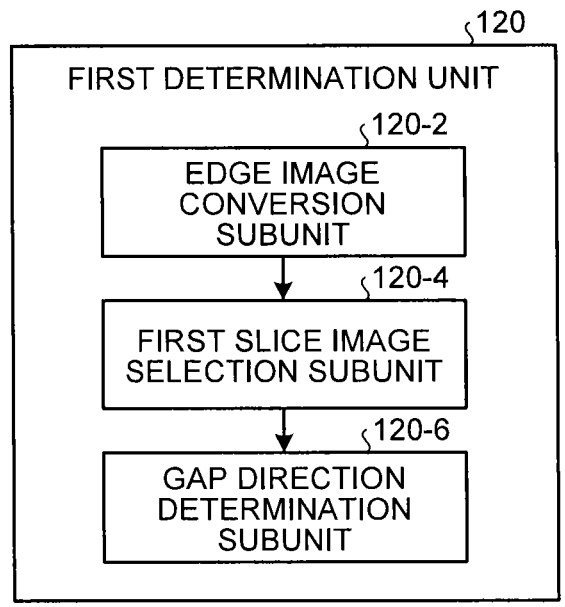
FIG. 3 is a block diagram illustrating an exemplary configuration of a first determination unit shown in FIG. 1 and FIG. 2.

A simplified summary of the present invention is given below to provide a basic understanding of some aspects of the present invention. It should be appreciated that the summary is not an exhaustive overview of the present invention, and is not intended to identify the key or critical parts of the present invention or limit the scope of the present invention, but merely to present some concepts in a simplified form as a prelude to the more detailed description that is discussed later.

It is a main object of the present invention to provide a scanning apparatus, a medical image device and a scanning method capable of positioning a leg scanning direction quickly and efficiently.

In accordance with an aspect of the present invention, there is provided a scanning apparatus including: a first scanning control unit configured to control a scanning operation performed on a leg to obtain at least one first slice image of the leg in an approximate coronal plane direction; a first determination unit configured to determine a direction of a gap between a thighbone and a shinbone in the at least one first slice image; a second scanning control unit configured to control a scanning operation performed on the leg to obtain at least one second slice image of the leg in a direction vertical to the direction of the gap in the at least one first slice image; a second determination unit configured to determine an axial plane direction according to the at least one second slice image; and a third scanning control unit configured to control a scanning operation performed on the leg to obtain at least one slice image of the leg in the axial plane direction.

In accordance with another aspect of the present invention, there is provided a medical image device which includes the aforementioned scanning apparatus.

In accordance with still another aspect of the present invention, there is provided a scanning method including the following steps of: controlling a scanning operation performed on a leg to obtain at least one first slice image of the leg in an approximate coronal plane direction; determining a direction of a gap between a thighbone and a shinbone in the at least one first slice image; controlling a scanning operation performed on the leg to obtain at least one second slice image of the leg in a direction vertical to the direction of the gap in the at least one first slice image; determining an axial plane direction according to the at least one second slice image; and controlling a scanning operation performed on the leg to obtain at least one slice image of the leg in the axial plane direction.

Furthermore, an embodiment of the present invention further provides a computer program for realizing the aforementioned method.

Additionally, an embodiment of the present invention further provides a computer program product in the form of a medium at least readable to a computer, on which computer program codes for realizing the aforementioned method are recorded.

These and other advantages of the present invention will be more apparent from the following detailed description of preferred embodiments of the present invention when read in conjunction accompanying drawings.

Preferred embodiments of the present invention are described below with reference to accompanying drawings. The elements and features described in one of the accompanying drawings or embodiments of the present invention may be combined with those shown in one or more other accompanying drawings or embodiments. It should be noted that for the sake of clarity, the presentation and description on the elements and processing that are irrelative with the present invention but well known by those skilled in the art are omitted.

FIG. 1 is a block diagram illustrating an exemplary configuration of a scanning apparatus 100 according to an embodiment of the present invention.

As shown in FIG. 1, the scanning apparatus 100 includes a first scanning control unit 110, a first determination unit 120, a second scanning control unit 130, a second determination unit 140 and a third scanning control unit 150.

The first scanning control unit 110 controls a scanning operation performed on a leg to obtain at least one first slice image of the leg in an approximate coronal plane direction. For example, the leg is blind scanned to obtain the at least one first slice image in the approximate coronal plane direction.

The first determination unit 120 determines the direction of the gap between a thighbone and a shinbone in the at least one first slice image. Information of the gap between the thighbone and the shinbone is contained in the at least one first slice image as obtained under the control of the first scanning control unit 110. The first determination unit 120 determines, according to the information of the gap between the thighbone and the shinbone, the direction of the gap in the first slice image.

The second scanning control unit 130 may control the scanning operation performed on the leg to obtain at least one second slice image of the leg in a direction vertical to the gap (that is, the direction of the gap in the at least one first slice image). It should be appreciated that the at least one second slice image in the direction vertical to the gap is also a slice image in an approximate sagittal plane direction.

The second determination unit 140 may determine an axial plane direction according to the at least one second slice image. In other words, the second determination unit 140 determines an axial plane direction according to the information contained in the second slice image.

The third scanning control unit 150 controls, according to the axial plane direction determined by the second determination unit 140, the scanning operation performed on the leg to obtain at least one slice image of the leg in the axial plane direction.

When the slice image in the axial plane direction is obtained, the slice image may be analyzed, synthesized and the like, as needed.

Actually, three planes, that is, a coronal plane, a sagittal plane and an axial plane, are imagined in anatomy so as to study a human body better. The coronal plane refers to a section dividing a human body into a front part and a back part along the front-back direction. The sagittal plane refers to a section dividing a human body into a left part and a right part along the left-right direction. The axial plane refers to a section dividing a human body into an upper part and a lower part along the up-down direction. However, the coronal plane, the sagittal plane and the axial plane desired to obtain may not necessarily be sections strictly defined as above but be sections which are similar to the coronal plane, the sagittal plane and the axial plane of a whole human body and present specific position relationships with a specific anatomical structure, that is, three sections in a position relationship similar to that among the coronal plane, the sagittal plane and the axial plane of a whole human body in a specific anatomical structure, depending upon the specific body part concerned or the specific anatomical structure. In other words, the coronal plane, the sagittal plane and the axial plane of a specific anatomical structure are not necessarily vertical to each other (but nearly vertical to each other to some extent) or necessarily parallel to the coronal plane, the sagittal plane and the axial plane of a whole human body. It is an object of the present invention to obtain at least one of specific axial plane, specific sagittal pane and specific coronal plane of a specific part (that is, knee) according to the specific anatomical structure of a leg. For instance, in a specific embodiment of the present invention, the direction of the plane vertical to the extension direction of the longest and/or straightest shinbone is determined as an axial plane direction. For instance, in a specific embodiment of the present invention, a coronal plane direction and a sagittal plane direction may be determined according to the PCL of the femoral cross section in a slice image in the axial plane direction. Further, the slice image in the axial plane direction (or sagittal plane direction or coronal plane direction) mentioned herein refers to the image of a slice parallel to the axial plane direction (or sagittal plane direction or coronal plane direction). As to the coronal plane direction employed by the first scanning control unit to obtain a first slice image, since the exact unique coronal plane direction of a specific leg structure is unknown during the initial scanning, the first scanning control unit has to control the scanning operation to obtain a first slice image of the leg in an approximate coronal plane direction, that is, the first slice image is the result of a "blind scanning". For example, the "approximate coronal plane direction" is roughly determined by the user during a blind scanning process according to the coronal plane direction of a whole human body without limitation.

FIG. 2 is a block diagram illustrating an exemplary configuration of a scanning apparatus 200 according to another embodiment of the present invention.

As shown in FIG. 2, the scanning apparatus 200 includes a first scanning control unit 110, a first determination unit 120, a second scanning control unit 130, a second determination unit 140, a third scanning control unit 150, a third determination unit 160 and a fourth scanning control unit 170. In other words, in addition to the components of the scanning apparatus 100 shown in FIG. 1, the scanning apparatus 200 shown in FIG. 2 further includes a third determination unit 160 and a fourth scanning control unit 170.

The first scanning control unit 110, the first determination unit 120, the second scanning control unit 130, the second determination unit 140 and the third scanning control unit 150 have been described in detail with reference to FIG. 1 and are therefore not described here repeatedly.

The third determination unit 160 determines a coronal plane direction and/or a sagittal plane direction according to the at least one slice image in the axial plane direction as obtained under the control of the third scanning control unit 150. In other words, the third determination unit 160 may only determine a coronal plane direction or a sagittal plane direction, or determine both a coronal plane direction and a sagittal plane direction, as needed.

The fourth scanning control unit 170 controls the scanning operation performed on the leg to obtain at least one slice image in the coronal plane direction by using the coronal plane direction determined by the third determination unit 160 and/or at least one slice image in the sagittal plane direction by using the sagittal plane direction determined by the third determination unit 160.

When the slice images in the axial plane direction, the sagittal plane direction and the coronal plane direction are obtained, the slice images may be analyzed, synthesized and the like, as needed.

In an example, at least one of the first scanning control unit 110, the second scanning control unit 130, the third scanning control unit 150, and the fourth scanning control unit 170 obtains a plurality of two-dimensional slice images by performing a multi-slice imaging or obtains one two-dimensional slice image.

For example, the multi-slice imaging is performed by controlling a magnetic resonance imaging (MRI) apparatus to execute a two-dimensional imaging sequence by which a plurality of two-dimensional slice images are obtained. Alternatively, for example, the multi-slice imaging is performed by controlling an MRI apparatus to execute a three-dimensional imaging sequence and to reconstruct a plurality of two-dimensional slice images based on magnetic resonance data acquired by the three-dimensional imaging sequence.

For example, the multi-slice imaging is performed by using a X-ray computed tomography (CT) apparatus which includes a multi-raw detector (which may be referred to as a "multi-slice detector" or a "multi-detector-row detector") that has a plurality of X-ray detecting elements arranged in a channel direction (a row direction) and in a slice direction (a column direction), and controlling the X-ray CT apparatus to obtain a plurality of two-dimensional slice images.

By processing two-dimensional slice images instead of three-dimensional slice images, the time spent on image processing is shortened, and a scanning direction is determined accurately even if the quality of the images is not high.

FIG. 3 is a block diagram illustrating an exemplary configuration of the first determination unit 120 shown in FIG. 1 and FIG. 2.

As shown in FIG. 3, the first determination unit 120 includes an edge image conversion subunit 120-2, a first slice image selection subunit 120-4 and a gap direction determination subunit 120-6.

The edge image conversion subunit 120-2 converts at least one first slice image into an edge image. Here, the first slice image may be converted into an edge image by using any proper method, for example, Sobel operator, Roberts operator, Prewitt operator or the Canny edge detector and like can all detect the edge of an image.

For instance, the edge in the first slice image can be detected by the Canny edge detector. In an example, the edge in the first slice image in a direction nearly vertical to the extension direction of the leg is detected by using the Canny edge detector. In other words, detection is not performed on the edge nearly parallel to the extension direction of the leg. The extension direction of the leg can be determined by using any proper method. An example of the determination on the extension direction of the leg will be described later with reference to FIG. 4.

In an example of the present invention, before the first slice image is converted into an edge image, the image of the knee joint part is extracted from the first slice image according to general features of knee joint. For instance, in the first slice image, the brightness of the knee joint part may be higher than other parts, so the image of the knee joint part can be roughly extracted according to brightness. Then, the edge in the image of the knee joint part in the direction nearly vertical to the extension direction of the leg is detected by, for example, the Canny edge detector, that is, the image of the knee joint part is converted into an edge image.

The first slice image selection subunit 120-4 selects a first slice image in which the gap between a thighbone and a shinbone is clear according to the edge distribution of the edge image. Since some edges are distributed substantially parallel to the gap between a thighbone and a shinbone at the position of the gap, the edge distribution is capable of reflecting the clearness of the gap between the thighbone and the shinbone. In other words, the more the edges distributed in this way are, the clearer the gap between the thighbone and the shinbone is.

The gap direction determination subunit 120-6 may determine the direction of the gap between the thighbone and the shinbone in the selected first slice image. For instance, the gap direction determination subunit 120-6 may further include an edge fitting module (not shown in FIG. 3) which is configured to fit points on the edge of the selected first slice image in a direction nearly vertical to the extension direction of the leg into a straight line representing the gap between the thighbone and the shinbone, the straight line representing the direction of the gap. Since the direction nearly vertical to the extension direction of the leg is also the extension direction of the gap between the thighbone and the shinbone, the edge in the direction nearly vertical to the extension direction of the leg contains information of the extension direction of the gap between the thighbone and the shinbone, therefore, a straight line representing the direction of the gap can be obtained by fitting points on the aforementioned edge.

Figure 4:
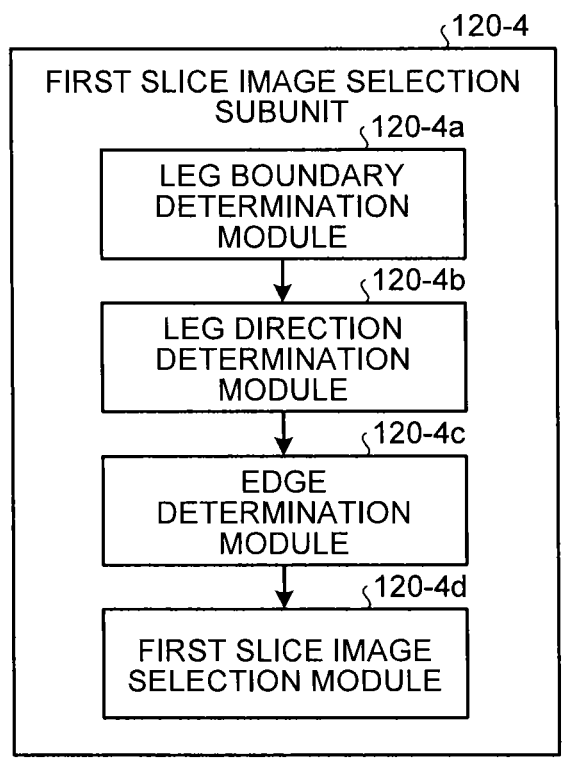
FIG. 4 is a block diagram illustrating an exemplary configuration of a first slice image selection subunit shown in FIG. 3.

FIG. 4 is a block diagram illustrating an exemplary configuration of the first slice image selection subunit 120-4 shown in FIG. 3.

As shown in FIG. 4, the first slice image selection subunit 120-4 includes a leg boundary determination module 120-4a, a leg direction determination module 120-4b, an edge determination module 120-4c and a first slice image selection module 120-4d.

The leg boundary determination module 120-4a may determine the boundaries of the leg on both sides. Leg information and background information may be both contained in the first slice image. Due to the obvious grayscale difference in the leg and the background, a proper threshold can be set to distinguish the leg and the background, and the boundaries on both sides of the leg as distinguished are the boundaries of the leg on both sides.

It can be easily appreciated that the boundaries of the leg on both sides can be obtained by using any other proper method but not limited to the method mentioned above.

The leg direction determination module 120-4b may determine the extension direction of the leg according to the boundaries of the leg on both sides. For example, a median line can be drawn according to the boundaries of the leg on both sides, the extension direction of the median line being the extension direction of the leg.

The edge determination module 120-4c may determine the edge distribution in a direction nearly vertical to the extension direction of the leg, since the edge distribution in a direction nearly vertical to the extension direction of the leg can reflect the general direction of the gap between the thighbone and the shinbone.

The more the edges distributed in the direction nearly vertical to the extension direction of the leg are, the clearer the gap between the thighbone and the shinbone is. The first slice image selection module 120-4d may select, as the first slice image in which the gap between the thighbone and the shinbone is clear, the first slice image having the highest edge distribution in the direction nearly vertical to the extension direction of the leg.

In an example of the present invention, the second determination unit 140 may determine an axial plane direction according to the shape of shinbone in the at least one second slice image. Preferably, the second determination unit 140 may determine the direction that is vertical to the extension direction of the longest and/or straightest shinbone in the at least one second slice image as an axial plane direction. Since the extension direction of the shinbone can reflect the extension direction of the leg, an axial plane direction can be determined according to the extension direction of the shinbone.

Figure 5:
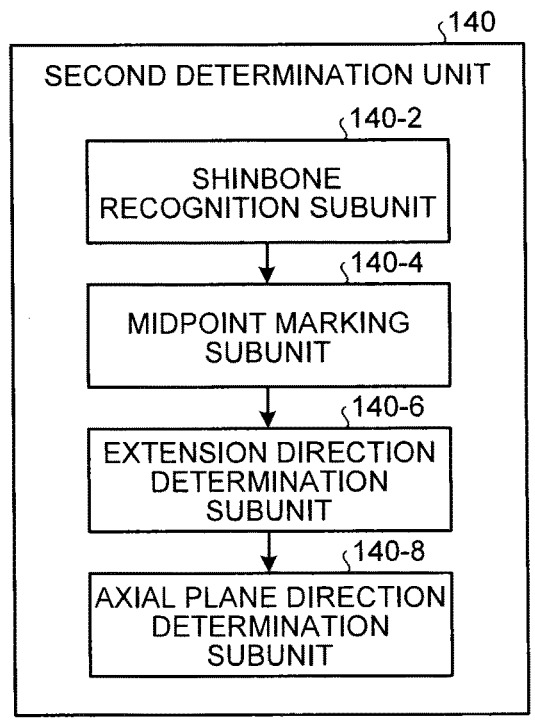
FIG. 5 is a block diagram illustrating an exemplary configuration of a second determination unit shown in FIG. 1 and FIG. 2.

FIG. 5 is a block diagram illustrating an exemplary configuration of the second determination unit 140 shown in FIG. 1 and FIG. 2.

As shown in FIG. 5, the second determination unit 140 includes a shinbone recognition subunit 140-2, a midpoint marking subunit 140-4, an extension direction determination subunit 140-6 and an axial plane direction determination subunit 140-8.

The shinbone recognition subunit 140-2 may recognize a shinbone in the at least one second slice image. In an example of the present invention, the second slice image can be converted, through a proper processing, into an image in which each tissue in the second slice image can be clearly distinguished, and the image resulting from the conversion is compared with a shinbone template to recognize the shinbone in each second slice image.

In another example of the present invention, a shinbone can be recognized through a logic analysis. For example, as the length-width ratio of a shinbone is different from those of other tissues, a shinbone can be recognized according to the length-width ratio of each tissue in the second slice image.

The midpoint marking subunit 140-4 may mark, in the extension direction of the recognized shinbone, a plurality of midpoints in the transverse direction of the shinbone at predetermined intervals.

The extension direction determination subunit 140-6 may determine the extension direction of the longest and/or straightest shinbone according to the plurality of midpoints marked by the midpoint marking subunit 140-4. Since information of length and straightness of a shinbone is contained in the plurality of midpoints marked by the midpoint marking subunit 140-4, the midpoints may be processed properly to obtain the information of length and straightness of the shinbone.

The axial plane direction determination subunit 140-8 determines the direction vertical to the extension direction of the longest and/or straightest shinbone as an axial plane direction.

Figure 6:
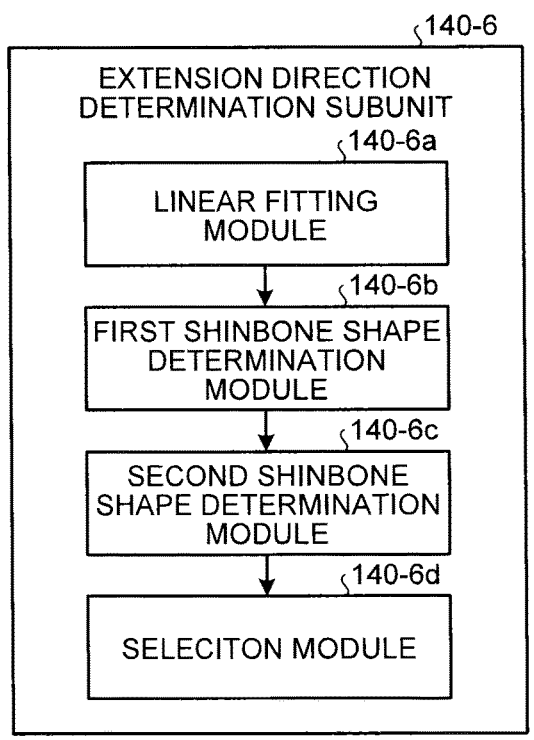
FIG. 6 is a block diagram illustrating an exemplary configuration of an extension direction determination subunit shown in FIG. 5.

FIG. 6 is a block diagram illustrating an exemplary configuration of the extension direction determination subunit 140-6 shown in FIG. 5.

As shown in FIG. 6, the extension direction determination subunit 140-6 may include a linear fitting module 140-6a, a first shinbone shape determination module 14-06b, a second shinbone shape determination module 14-06c and a selection module 140-6d.

The linear fitting module 140-6a may perform a linear fitting on the plurality of midpoints marked by the midpoint marking subunit 140-4 to obtain a fitted straight line representing the extension direction of the shinbone.

The first shinbone shape determination module 140-6b determines the length of the shinbone according to the number of the midpoints passing through the fitted straight line. For instance, the more the midpoints passing through the fitted straight line are, the longer the shinbone is. Alternatively, the more the midpoints spaced away from the fitted straight line by a distance smaller than a predetermined threshold are, the longer the shinbone is. Therefore, the number of the midpoints passing through the fitted straight line can reflect the length of the shinbone.

The second shinbone shape determination module 140-6c may determine the straightness of the shinbone according to the spatial distribution of the plurality of midpoints marked by the midpoint marking subunit 140-4 with respect to the fitted straight line representing the extension direction of the shinbone. For example, the shorter the distance between the plurality of midpoints and the fitted straight line is, the straighter the shinbone is. The number of the midpoints above further reflects the straightness of the shinbone in addition to the length of the shinbone.

The selection module 140-6d may select a second slice image containing the longest and straightest shinbone image from the at least one second slice image according to the length and straightness of the shinbone. In other words, the selection module may select a second slice image containing the longest and straightest shinbone image from the at least one slice image by synthesizing the length and the straightness of shinbone images. For example, a second slice image containing the straightest shinbone image may be selected from a plurality of second slice images containing longer shinbone images. Alternatively, a second slice image containing the longest shinbone image may be selected from a plurality of second slice images containing straighter shinbone images.

However, it should be easily appreciated that apart from the linear fitting module 140-6a and the selection module 140-6d, the extension direction determination subunit 140-6 may include only one of the first shinbone shape determination module 140-6b and the second shinbone shape determination module 140-6c.

If the extension direction determination subunit 140-6 only includes the linear fitting module 140-6a, the first shinbone shape determination module 140-6b and the selection module 140-6d, the selection module 140-6d may select the second slice image containing the longest shinbone image from the at least one second slice image according to the shinbone length in each second slice image determined by the first shinbone shape determination module 140-6b.

If the extension direction determination subunit 140-6 only includes the linear fitting module 140-6a, the second shinbone shape determination module 140-6c and the selection module 140-6*d*, the selection module 140-6*d* may select the second slice image containing the straightest shinbone image from the at least one second slice image according to the straightness of the shinbone determined by the second shinbone shape determination module 140-6*c*.

In an example of the present invention, the third determination unit 160 shown in FIG. 2 determines a coronal plane direction and/or a sagittal plane direction according to the PCL of the femoral cross section in the at least one slice image in the axial plane direction. The femoral cross section is M-shaped, and the straight line tangent to the lower end of the M shape is called a PCL. Since there exists a specific position relationship between the coronal plane direction/the sagittal plane direction and the PCL, the coronal plane direction and the sagittal plane direction can be determined according to the PCL.

Figure 7:
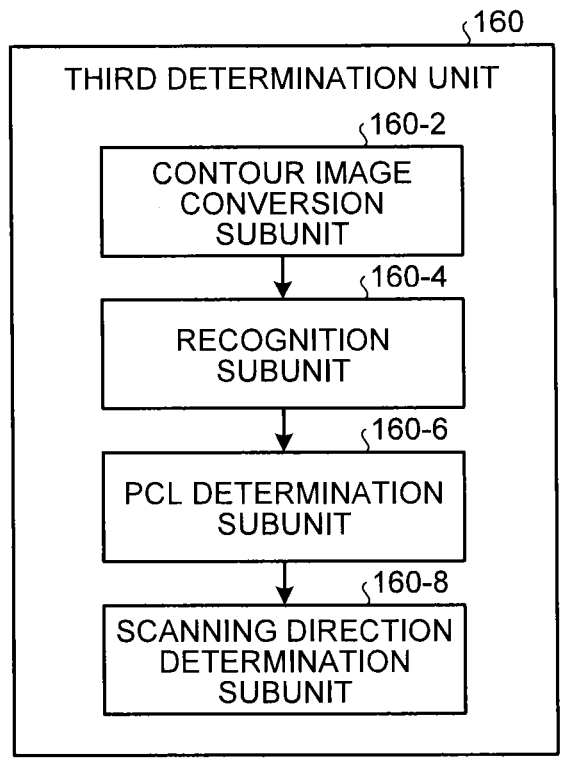
FIG. 7 is a block diagram illustrating an exemplary configuration of a third determination unit shown in FIG. 2.

FIG. 7 is a block diagram illustrating an exemplary configuration of the third determination unit 160 shown in FIG. 2.

As shown in FIG. 7, the third determination unit 160 includes a contour image conversion subunit 160-2, a recognition subunit 160-4, a PCL determination subunit 160-6 and a determination subunit 160-8.

The contour image conversion subunit 160-2 converts at least one slice image in the axial plane direction into a contour image. Preferably, the contour image conversion subunit 160-2 divides the at least one slice image in the axial plane direction into a plurality of parts based on Graph theory and converts the image as divided into a contour image. Specifically, the slice image in the axial plane direction can be represented as a graph which includes sides and vertexes, each side representing the position of a pixel as well as the relationship between the pixel and an adjacent pixel, each vertex representing the contrast ratio of a pixel to an adjacent pixel. Graphs are sorted in ascending order of the height of the vertexes thereof. Adjacent pixels are combined in ascending order of the height of the vertexes, thereby obtaining each part in the slice image in the axial plane direction. The combination is stopped if the vertex is higher than a predetermined threshold, which may be set based on experience. Through the processing above, the slice image in the axial plane direction is divided into a plurality of parts.

Further, the image as divided can be converted into the contour images by using any proper method, for example, using a priori knowledge method, a mathematical morphology method, a gradient-based method, a level set method, an active contour model and a neurodynamics method.

The recognition subunit 160-4 may compare the contour image with a femoral cross section template to recognize the femoral cross section that is most similar to the femoral cross section template.

Preferably, the recognition subunit 160-4 may compare the contour image with the femoral cross section template based on shape context to recognize the femoral cross section that is most similar to the femoral cross section template.

In a shape matching, the similarity between two objects is usually compared to determine whether or not the two objects are matched in shape. Shape context is capable of describing the features of an object well and measuring the similarity between the boundary contour information of two objects.

Specifically, if there are n points in an image, then a position relationship exists between a certain point Pi and each one of the other n−1 points, which leads to the generation of n−1 vectors. The information described by the n−1 vectors determines the shape feature of the object. The greater the n is, the more information amount is, and the more accurate the description is. By describing two objects to be compared and comparing the similarity between the two described objects in this way, whether or not the two objects are matched with each other can be determined.

Certainly, the contour image can be compared with the femoral cross section template by using a curvature-based contour matching algorithm and a Douglas-Peucker based contour matching algorithm and any other proper method, but the method is not limited to the method based on shape context.

The posterior condylar line determination subunit 160-6 may determine a PCL according to the femoral cross section that is most similar to the femoral cross section template. Specifically, a tangent line, which is detected below the shape 'M' that is presented in the femoral cross section that is most similar to the template, is a PCL.

The scanning direction determination subunit 160-8 may determine the plane parallel to the PCL and vertical to the axial plane as the coronal plane and/or determine the plane parallel to a line, which forms a predetermined angle with the PCL, and vertical to the axial plane as the sagittal plane.

In other words, the scanning direction determination subunit 160-8 may only determine the plane parallel to the PCL and vertical to the axial plane as the coronal plane or the plane parallel to a line, which forms a predetermined angle with the PCL, and vertical to the axial plane as the sagittal plane, or performs the two operations at the same time, as needed.

For instance, different predetermined angles are set for the left leg and the right leg based on physiological features.

Figure 8:
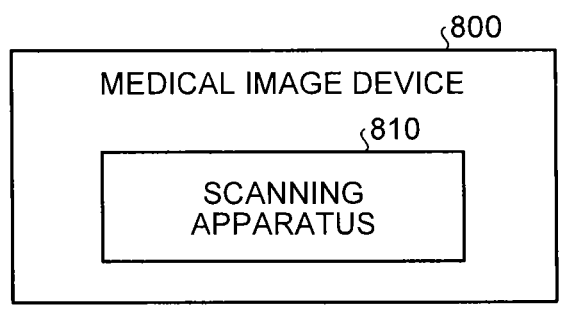
FIG. 8 is a block diagram illustrating an exemplary configuration of a medical image device according to an embodiment of the present invention.

FIG. 8 is a block diagram illustrating an exemplary configuration of a medical image device 800 according to an embodiment of the present invention.

In order not to obscure the spirit and scope of the present invention, other possible members of the medical image device 800 are saved in FIG. 8. The medical image device 800 may include a scanning apparatus 810, which may be the scanning apparatus 100 or 200. The medical image device 800 may be, but not limited to: an X-ray imaging diagnostic apparatus, an ultrasound (UL) diagnostic imaging apparatus, a X-ray computed tomography (CT) apparatus, a magnetic resonance imaging (MRI) apparatus, a positron emission tomography (PET) apparatus and the like.

Specific way or manner, in which the aforementioned scanning apparatus may be arranged in a medical image device, is well known by those skilled in the art and is therefore not repeatedly described herein.

Some processing or methods are also apparently disclosed during the process of describing the scanning apparatus according to the aforementioned embodiments. Below, these methods are described roughly without repeating some details which are already discussed above, however, it should be noted that although disclosed during the process of describing the scanning apparatus, the methods does not necessarily employ the components or are necessarily performed by the components. For instance, embodiments of the scanning apparatus may be partially or completely achieved by hardware and/or firmware, and the scanning method described below may be fully achieved by a computer-executable program FIG. 9 is a flowchart of a scanning method according to an embodiment of the present invention.

Figure 9:
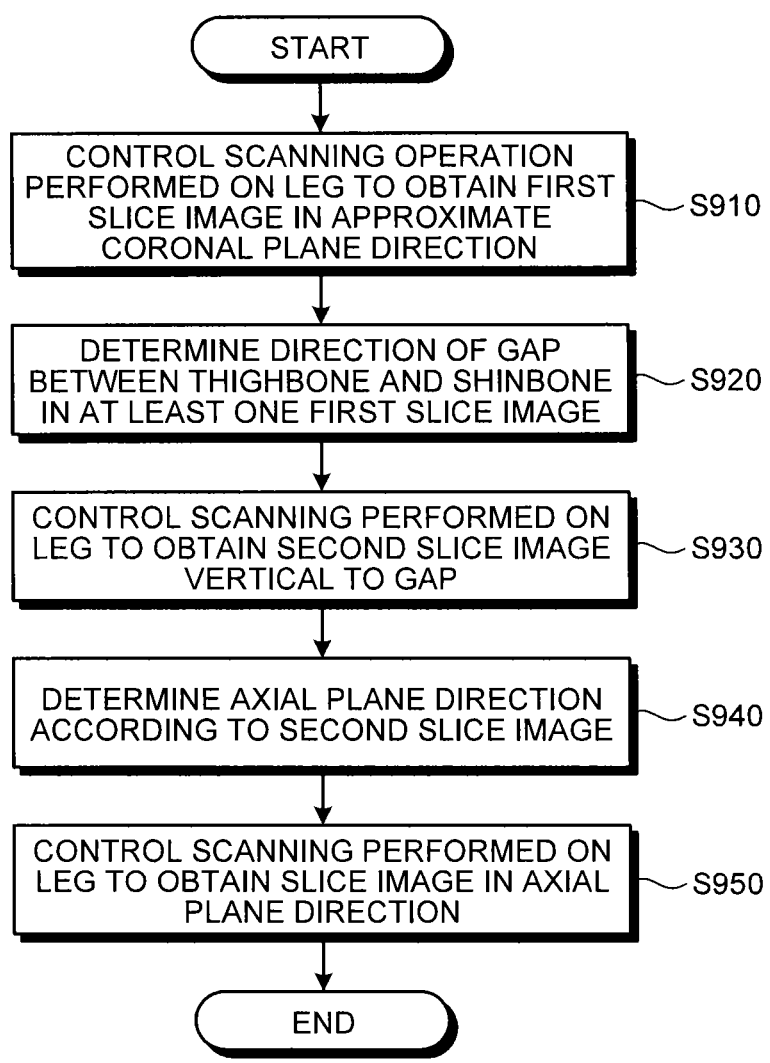
FIG. 9 is a flowchart of a scanning method according to an embodiment of the present invention.

As shown in FIG. 9, in Step S910, the scanning operation performed on a leg is controlled to obtain at least one first slice image of the leg in an approximate coronal plane direction. For instance, Step S910 may be performed by the first scanning control unit 110 described with reference to FIG. 1 and FIG. 2.

In Step S920, the direction of the gap between a thighbone and a shinbone in the at least one first slice image is determined. For instance, Step S920 may be performed by the first determination unit 120 described with reference to FIG. 1 and FIG. 2.

In Step S930, the scanning operation performed on the leg is controlled to obtain at least one second slice image of the leg in a direction vertical to the gap (that is, the direction of the gap in the at least one first slice image). For instance, Step S930 may be performed by the second scanning control unit 130 described with reference to FIG. 1 and FIG. 2.

In Step S940, an axial plane direction is determined according to the at least one second slice image. For instance, Step S940 may be performed by the second determination unit 140 described with reference to FIG. 1 and FIG. 2.

In Step S950, the scanning operation performed on the leg is controlled to obtain at least one slice image of the leg in the axial plane direction. For instance, Step S950 may be performed by the third scanning control unit 150 described with reference to FIG. 1 and FIG. 2.

Figure 10:
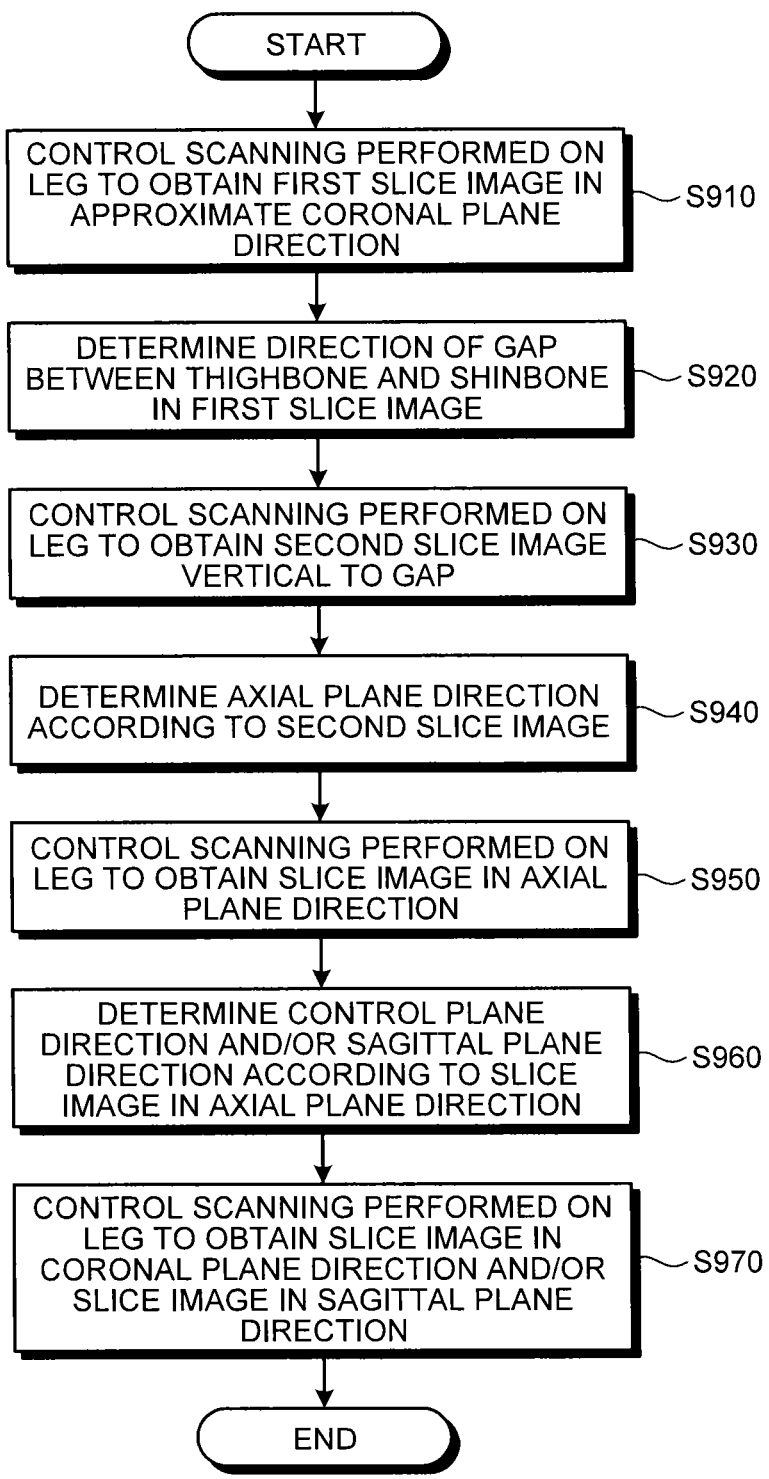
FIG. 10 is a flowchart of a scanning method according to another embodiment of the present invention.

FIG. 10 is a flowchart of a scanning method according to another embodiment of the present invention.

Steps S910-S950 of the scanning method shown in FIG. 10 are the same as Steps S910-S950 of the scanning method shown in FIG. 9 and are therefore not described here repeatedly.

In Step S960, a coronal plane direction and/or a sagittal plane direction are/is determined according to the at least one slice image in the axial plane direction. For instance, Step S960 may be performed by the third determination unit 160 described with reference to FIG. 2.

In Step S970, the scanning operation performed on the leg is controlled to obtain at least one slice image in the coronal plane direction and/or at least one slice image in the sagittal plane direction. For instance, Step S970 may be performed by the fourth scanning control unit 170 described with reference to FIG. 2.

Figure 11:
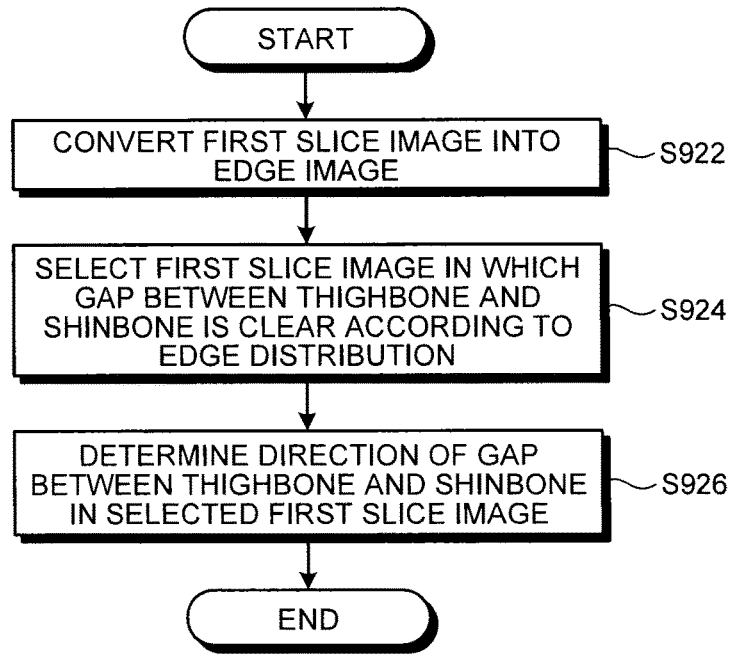
FIG. 11 is a flowchart illustrating an exemplary process of Step S920 shown in FIG. 9 and FIG. 10.

FIG. 11 is a flowchart illustrating an exemplary processing of Step S920 (that is, the determination on the direction of the gap between the thighbone and the shinbone in the at least one first slice image) shown in FIG. 9 and FIG. 10.

As shown in FIG. 11, in Step S922, the at least one first slice image is converted into an edge image. For instance, Step S922 may be performed by the edge image conversion subunit 120-2 described with reference to FIG. 3.

In Step S924, a first slice image in which the gap between the thighbone and the shinbone is clear is selected according to the edge distribution of the edge image. For instance, Step S924 may be performed by the first slice image selection subunit 120-4 described with reference to FIG. 3.

Specifically, the boundaries of the leg on both sides are determined first. Then, the extension direction of the leg is determined according to the boundaries of the leg on both sides. Then, the edge distribution in a direction nearly vertical to the extension direction of the leg is determined. Last, the first slice image having the highest edge distribution in the direction nearly vertical to the extension direction of the leg is selected as the first slice image in which the gap between the thighbone and the shinbone is clear.

In Step S926, the direction of the gap between the thighbone and the shinbone in the selected first slice image is determined. For instance, Step S926 may be performed by the gap direction determination subunit 120-6 described with reference to FIG. 3.

Specifically, points on the edge of the selected first slice image in the direction nearly vertical to the extension direction of the leg is fitted into a straight line representing the gap between the thighbone and the shinbone, the straight line representing the direction of the gap.

In Step S940 shown in FIG. 9 and FIG. 10 (that is, the step of determining an axial plane direction according to the at least one second slice image), an axial plane direction can be determined according to the shape of shinbone in the at least one second slice image. Preferably, the direction that is vertical to the extension direction of the longest and/or straightest shinbone in the at least one second slice image is determined as an axial plane direction.

Figure 12:
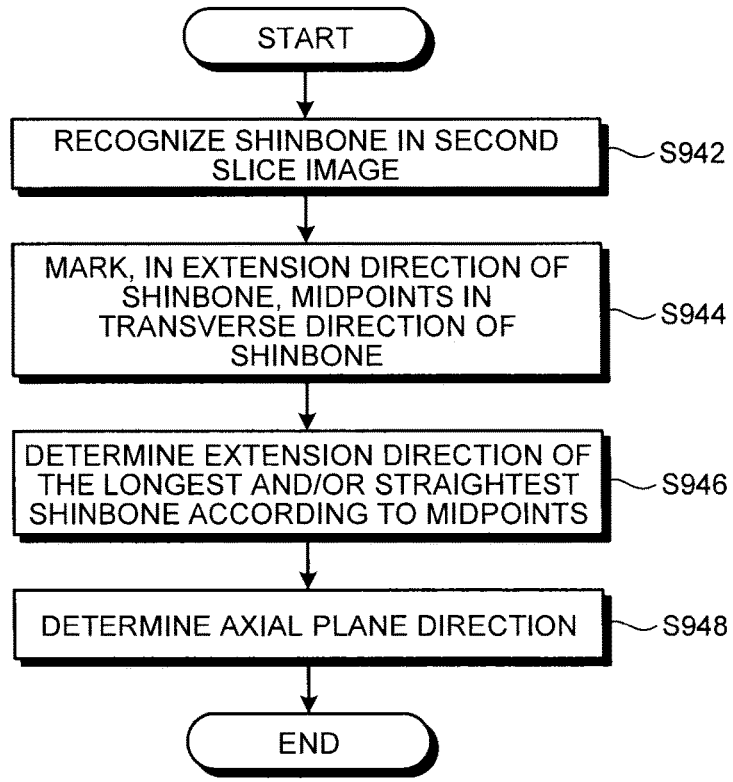
FIG. 12 is a flowchart illustrating an exemplary process of Step S940 shown in FIG. 9 and FIG. 10.

FIG. 12 is a flowchart illustrating an exemplary process of Step S940 shown in FIG. 9 and FIG. 10.

As shown in FIG. 12, in Step S942, a shinbone is recognized in the at least one second slice image. For instance, Step S942 may be performed by the shinbone recognition subunit 140-2 described with reference to FIG. 5.

In Step S944, a plurality of midpoints in the transverse direction of the shinbone are marked in the extension direction of the shinbone at predetermined intervals. Step S944 may be performed by the midpoint marking subunit 140-2 described with reference to FIG. 5.

In Step S946, the extension direction of the longest and/or straightest shinbone is determined according to the plurality of midpoints. Step S946 may be performed by the extension direction determination subunit 140-6 described with reference to FIG. 5.

In Step S948, the direction that is vertical to the extension direction of the longest and/or straightest shinbone is determined as an axial plane direction. Step S948 may be performed by the axial plane direction determination subunit 140-8 described with reference to FIG. 5.

In an example, a plurality of midpoints are linearly fitted to obtain a fitted straight line representing the extension direction of a shinbone, the length of the shinbone is determined according to the number of the midpoints passing through the fitted straight line, and the second slice image containing the longest shinbone image is selected from the at least one second slice image.

In another example, a plurality of midpoints are linearly fitted to obtain a fitted straight line representing the extension direction of a shinbone, the straightness of the shinbone is determined according to the spatial distribution of the plurality of midpoints with respect to the fitted straight line representing the extension direction of the shinbone, and the second slice image containing the straightest shinbone image is selected from the at least one second slice image according to the straightness of shinbones.

In still another example, the plurality of midpoints are linearly fitted to obtain a fitted straight line representing the extension direction of a shinbone, the length of the shinbone is determined according to the number of the midpoints passing through the fitted straight line, and the straightness of the shinbone is determined according to the spatial distribution of the plurality of midpoints with respect to the fitted straight line representing the extension direction of the shinbone, and the second slice image containing the longest and straightest shinbone image is selected from the at least one second slice image according to the length and straightness of shinbones.

In Step S960 shown in FIG. 10 (that is, the step of determining a coronal plane direction and/or a sagittal plane direction according to the at least one slice image in the axial plane direction), a coronal plane direction and/or a sagittal plane direction are/is determined according to the PCL of the femoral cross section in the at least one slice image in the axial plane direction.

Figure 13:
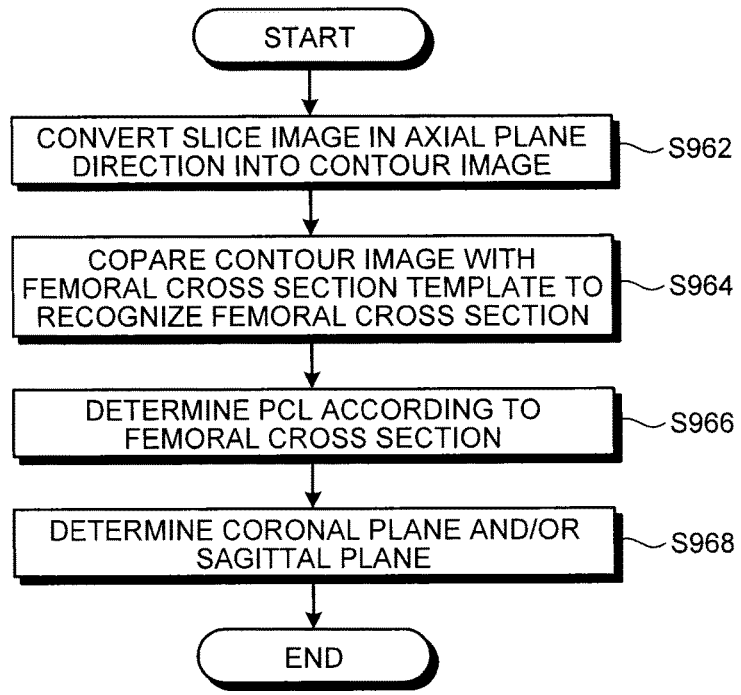
FIG. 13 is a flowchart illustrating an exemplary process of Step S960 shown in FIG. 10.

FIG. 13 is a flowchart illustrating an exemplary process of Step S960 shown in FIG. 10.

As shown in FIG. 13, in Step S962, the at least one slice image in the axial plane direction is converted into a contour image. For instance, Step S962 may be performed by the contour image conversion subunit 160-2 described with reference to FIG. 7.

For example, preferably, each part of the at least one slice image in the axial plane direction is divided based on graph theory, and the image as divided are converted into a contour image by using a proper method.

In Step S964, the contour image is compared with a femoral cross section template to recognize the femoral cross section that is most similar to the femoral cross section template. For instance, Step S964 may be performed by the recognition subunit 160-4 described with reference to FIG. 7.

For example, preferably, the contour image is compared with the femoral cross section template based on shape context to recognize the femoral cross section that is most similar to the femoral cross section template.

In Step S966, a PCL is determined according to the femoral cross section that is most similar to the femoral cross section template. For instance, Step S966 may be performed by the posterior condylar line determination subunit 160-6 described with reference to FIG. 7.

In Step S968, the plane parallel to the PCL and vertical to the axial plane is determined as the coronal plane, and/or the plane parallel to a line, which forms a predetermined angle with the PCL, and vertical to the axial plane is determined as the sagittal plane. For instance, Step S968 may be performed by the determination subunit 160-8 described with reference to FIG. 7.

As an example, each step of the aforementioned scanning method and each module and/or unit of the aforementioned scanning apparatus may be implemented as software, firmware, hardware or the combination thereof. In the case where the steps or modules and/or units are achieved through software or firmware, a software program for realizing the aforementioned method is installed in a computer with a specific hardware structure (e.g. the general computer 1400 shown in FIG. 14) from a storage medium or network, and the computer, when installed with a program, is capable of realizing the functions of the program.

Figure 14:
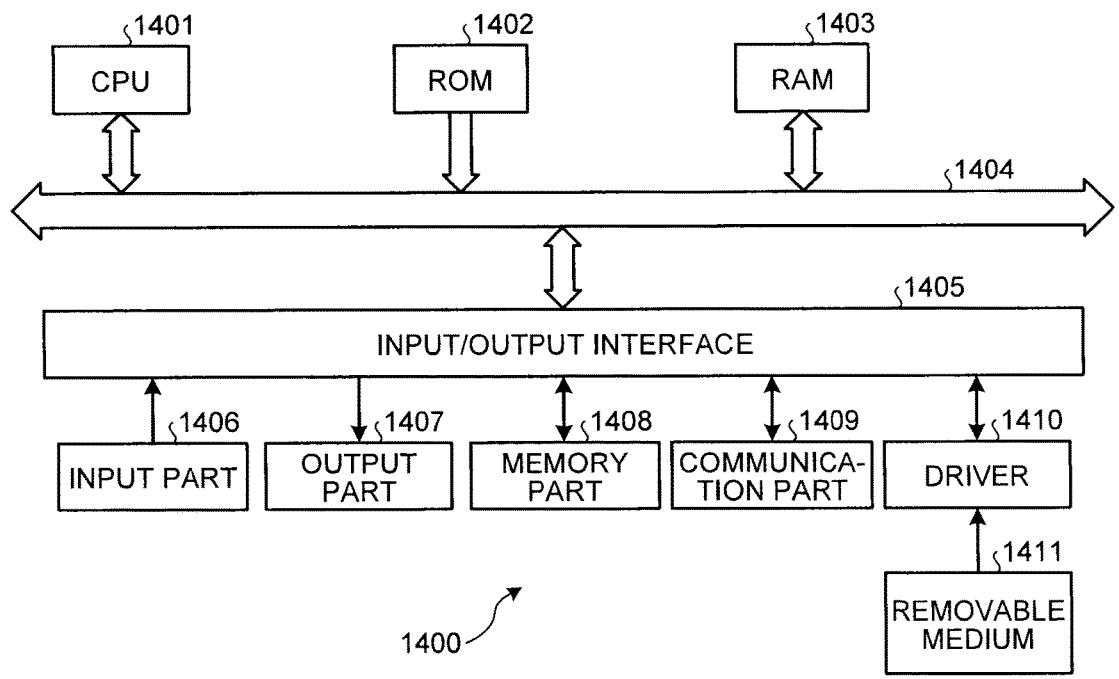
FIG. 14 is a diagram showing an exemplary structure of a computing device for realizing the scanning apparatus and method of the invention.

In FIG. 14, an operation processing unit (namely, CPU) 1401 executes various processing via a program stored in a read-only memory (ROM) 1402 or a program loaded to a random access memory (RAM) 1408 from a memory part 1403. The data needed for the various processing of the CPU 1401 may be stored in the RAM 1403 as needed. CPU 1401, ROM 1402 and RAM 1403 are linked with each other via a bus 1404, with which an input/output 1405 is also connected.

The following members are linked with the input/output interface 1405, an input part 1406 (including keyboard, mouse and the like), an output part 1407 (including displays such as cathode ray tube (CRT), liquid crystal display (LCD) and loudspeaker), a memory part 1408 (including hard disc and the like), and a communication part 1409 (including a network interface card such as LAN card and modem). The communication part 1409 realizes a communication via a network such as the Internet. A driver 1410 may also be connected with the input/output interface 1405, if needed. If needed, a removable medium 1411, for example, a magnetic disc, an optical disc, a magnetic optical disc, a semiconductor memory and the like, may be installed in the driver 1410 to read a computer program therefrom and install the read computer program in the memory part 1408.

In the case where the foregoing series of processing is achieved through software, programs forming the software are installed from a network such as the Internet or a storage medium such as the removable medium 1411.

It should be appreciated by those skilled in the art that the storage medium is not limited to the detachable medium 1411 shown in FIG. 14, which is distributed separated from the apparatus so as to provide the programs for users. The detachable medium 1411 may be, for example, a magnetic disc (including floppy disc (registered trademark)), a compact disc (including compact disc read-only memory (CD-ROM) and digital video disc (DVD), a magneto optical disc (including mini disc (MD)(registered trademark))), and a semiconductor memory. Alternatively, the storage mediums may be the hard discs included in ROM 1402 and the memory part 1408, and programs are stored in the storage medium and can be distributed to users along with the storage medium.

The present invention further discloses a program product in which machine-readable instruction codes are stored. The scanning method described herein can be implemented when the instruction codes are read and performed by a machine.

Accordingly, a memory medium for storing the program product in which computer-readable instruction codes are stored is also included in the present invention. The storage medium includes, but is not limited to: soft disc, optical disc, magnetic optical disc, memory card, memory stick and the like.

In the foregoing description on the specific embodiments of the present invention, the features described and/or shown for an implementation mode may be used in one or more other implementation modes in the same or like way or combined with the those of the other implementation modes, or replace those of the other implementation modes.

It should be emphasized that the terms "comprise/include", as used herein, means the existence of a feature, element, step or component in a way not exclusive of the existence or addition of one or more other features, elements, steps or components.

In the aforementioned embodiments and examples, each step and/or unit is represented with a reference sign consisting of figures. It should be understood by those of ordinary skill of the art that the reference signs are merely intended to facilitate description and drawing but are not to be construed as a limitation on an order or any other aspect.

Furthermore, the methods provided in the present invention may be performed sequentially, synchronously or independently in accordance with another time sequences, not limited the time sequence described herein. Therefore, the implementation orders of the methods described in this specification are not to be construed as a limitation to the scope of the present invention.

Although the present invention has been disclosed with reference to specific embodiments herein, it should be understood that all the implementation modes and examples described above are merely illustrative of the present invention but are not to be construed as limiting the present invention. Various modifications, improvements or equivalents can be devised by those skilled in the art without departing from the spirit and scope of the invention, and such modifications, improvements or equivalents should be considered to be within the scope of the present invention.

What is claimed is:

1. A scanning apparatus, comprising:
   a medical imaging apparatus configured to perform scanning operations on a leg;
   processing circuitry configured to:
   control a first scanning operation performed by the medical imaging apparatus on the leg to obtain at least one first slice image of the leg in an approximate coronal plane direction;
   determine a direction along a line passing through a gap between a thighbone and a shinbone in the at least one first slice image;
   control a second scanning operation performed by the medical imaging apparatus on the leg to obtain at least one second slice image of a sagittal plane of the leg in a direction vertical to the direction along the line passing through the gap in the at least one first slice image;
   determine an axial plane direction according to a shape of a shinbone in the at least one second slice image, wherein to determine the axial plane direction, the processing circuitry is further configured to,
   recognize the shinbone from the at least one second slice image,
   mark, in an extension direction of the shinbone, a plurality of midpoints in a transverse direction of the shinbone at predetermined intervals,
   determine the extension direction of the longest and/or straightest shinbone according to the plurality of midpoints, and
   determine a direction vertical to the extension direction of the longest and/or straightest shinbone as the axial plane direction; and
   control a third scanning operation performed by the medical imaging apparatus on the leg to obtain at least one slice image of the leg in the axial plane direction.

2. The scanning apparatus according to claim 1, wherein the processing circuitry is further configured to
   determine a coronal plane direction and/or a sagittal plane direction according to the at least one slice image in the axial plane direction; and
   control a scanning operation performed on the leg to obtain at least one slice image in the coronal plane direction and/or at least one slice image in the sagittal plane direction.

3. The scanning apparatus according to claim 1, wherein the processing circuitry is configured to
   convert the at least one first slice image into an edge image;
   select a first slice image in which the gap between the thighbone and the shinbone is clear according to an edge distribution of the edge image; and
   determine the direction of along the line passing through the gap between the thighbone and the shinbone in the selected first slice image.

4. The scanning apparatus according to claim 3, wherein the processing circuitry is configured to
   determine the boundaries of the leg on both sides;
   determine an extension direction of the leg according to the boundaries of the leg on both sides;
   determine an edge distribution in a direction nearly vertical to the extension direction of the leg; and
   select, as the first slice image in which the gap between the thighbone and the shinbone is clear, a first slice image having the highest edge distribution in the direction nearly vertical to the extension direction of the leg.

5. The scanning apparatus according to claim 3, wherein the processing circuitry is configured to fit points on an edge of the selected first slice image in a direction nearly vertical to the extension direction of the leg into a straight line representing the gap between the thighbone and the shinbone, the straight line representing the direction along the line passing through the gap in the at least one first slice image.

6. The scanning apparatus according to claim 1, wherein the processing circuitry is configured to
   perform a linear fitting on the plurality of midpoints to obtain a fitted straight line representing the extension direction of the shinbone;
   determine a length of the shinbone according to the number of the midpoints passing through the fitted straight line; and
   select, from the at least one second slice image, a second slice image containing the longest shinbone image.

7. The scanning apparatus according to claim 1, wherein the processing circuitry is configured to
   perform a linear fitting on the plurality of midpoints to obtain a fitted straight line representing the extension direction of the shinbone;
   determine the straightness of the shinbone according to the spatial distribution of the plurality of midpoints with respect to the fitted straight line representing the extension direction of the shinbone; and
   select, from the at least one second slice image, a second slice image containing the straightest shinbone image according to the straightness of the shinbone.

8. The scanning apparatus according to claim 1, wherein the processing circuitry is configured to
   perform a linear fitting on the plurality of midpoints to obtain a fitted straight line representing the extension direction of the shinbone;
   determine the length of the shinbone according to the number of the midpoints passing through the fitted straight line;
   determine the straightness of the shinbone according to the spatial distribution of the plurality of midpoints with respect to the fitted straight line representing the extension direction of the shinbone; and
   select, from the at least one slice image, the second slice image containing the longest and straightest shinbone image according to the length and straightness of shinbone.

9. The scanning apparatus according to claim 2, wherein the processing circuitry is configured to determine the coronal plane direction and/or the sagittal plane direction according to the posterior condylar line of the femoral cross section in the at least one slice image in the axial plane direction.

10. The scanning apparatus according to claim 9, wherein the processing circuitry is configured to
    convert at least one slice image in the axial plane direction into a contour image;
    compare the contour image with a femoral cross section template to recognize the femoral cross section that is most similar to the femoral cross section template;
    determine the posterior condylar line according to the femoral cross section that is most similar to the femoral cross section template; and
    determine a direction parallel to the posterior condylar line and vertical to the axial plane direction as the coronal plane direction and/or determine a direction parallel to a line, which forms a predetermined angle with the posterior condylar line, and vertical to the axial plane direction as the sagittal plane direction.

11. The scanning apparatus according to claim 10, wherein the processing circuitry is configured to divide, based on graph theory, the at least one slice image in the axial plane direction into a plurality of parts and convert the image after being divided into a contour images.

12. The scanning apparatus according to claim 10, wherein the processing circuitry is configured to compare, based on shape context, the contour image with the femoral cross section template to recognize the femoral cross section that is most similar to the femoral cross section template.

* * * * *